(12) United States Patent
McDevitt et al.

(10) Patent No.: US 10,060,937 B2
(45) Date of Patent: Aug. 28, 2018

(54) INTEGRATED INSTRUMENTATION FOR THE ANALYSIS OF BIOFLUIDS AT THE POINT-OF-CARE

(71) Applicant: William Marsh Rice University, Houston, TX (US)

(72) Inventors: John McDevitt, Houston, TX (US); Ahmed Haque, Houston, TX (US); Michael McRae, Houston, TX (US); Glen Simmons, Houston, TX (US)

(73) Assignee: William Marsh Rice University, Houston, TX (US)

( * ) Notice: Subject to any disclaimer, the term of this patent is extended or adjusted under 35 U.S.C. 154(b) by 837 days.

(21) Appl. No.: 14/319,497

(22) Filed: Jun. 30, 2014

(65) Prior Publication Data

US 2015/0004717 A1    Jan. 1, 2015

Related U.S. Application Data

(60) Provisional application No. 61/841,090, filed on Jun. 28, 2013.

(51) Int. Cl.
*G01N 35/10* (2006.01)
*G01N 35/00* (2006.01)

(52) U.S. Cl.
CPC ... *G01N 35/00029* (2013.01); *G01N 35/1002* (2013.01); *G01N 2035/00039* (2013.01); *G01N 2035/00148* (2013.01)

(58) Field of Classification Search
CPC ............ G01N 35/00029; G01N 35/00; G01N 35/1002; G01N 35/10

USPC ......................................... 422/63, 50; 436/43
See application file for complete search history.

(56) References Cited

U.S. PATENT DOCUMENTS

| | | | | |
|---|---|---|---|---|
| 5,374,395 A | * | 12/1994 | Robinson | G01N 21/253 422/562 |
| 2006/0257991 A1 | * | 11/2006 | McDevitt | C12M 41/36 435/287.2 |
| 2007/0265730 A1 | * | 11/2007 | Greyshock | G06K 7/14 700/236 |
| 2009/0215072 A1 | | 8/2009 | McDevitt | |
| 2011/0132163 A1 | * | 6/2011 | Deutsch | B26D 5/007 83/78 |
| 2012/0322682 A1 | | 12/2012 | McDevitt | |
| 2013/0130933 A1 | | 5/2013 | McDevitt | |

FOREIGN PATENT DOCUMENTS

| | | |
|---|---|---|
| WO | 2005083423 | 10/2005 |
| WO | 2005085796 | 1/2006 |
| WO | 2007134189 | 7/2008 |
| WO | 2007002480 | 3/2009 |

(Continued)

OTHER PUBLICATIONS

Christodoulides, N. et al., "A microchip-based multianalyte system for the assessment of cardiac risk," Anal Chem. 74(13), 3030-3036 (2002).

(Continued)

*Primary Examiner* — Christine T Mui
(74) *Attorney, Agent, or Firm* — Boulware & Valoir

(57) ABSTRACT

This disclosure describes the design and function of a bead-based lab-on-a-chip portable analyzer for analyzing biomarker assay cards used in point-of-care testing.

26 Claims, 12 Drawing Sheets

(56) References Cited

FOREIGN PATENT DOCUMENTS

| WO | 2012021714 | 4/2012 |
|---|---|---|
| WO | 2012065025 | 7/2012 |
| WO | 2012154306 | 11/2012 |
| WO | 2012065117 | 4/2014 |

OTHER PUBLICATIONS

Christodoulides, et al., "Programmable Bio-nano-chip Technology for the Diagnosis of Cardiovascular Disease at the Point-of-care,"Method. De Bakey Cardiovasc. J., 1, 6 (2012).

Christodoulides, N., et al., "A microchip-based assay for interleukin-6," Meth. Mol. Bio. 385, 131-144 (2007).

Christodoulides, N., et al., "Application of microchip assay system for the measurement of C-reactive protein in human saliva," Lab Chip. 5(3), 261-269 (2005).

Floriano, P.N., et al., "Membrane-based on-line optical analysis system for rapid detection of bacteria and spores," Biosens Bioelectron. 20(10), 2079-2088 (2005).

Goodey, A. et al., "Development of multianalyte sensor arrays composed of chemically derivatized polymeric microspheres localized in micromachined cavities," J. Am. Chem. Soc. 123, 2559-2570 (2001).

Jokerst J.V., et al., "Programmable nano-bio-chips: multifunctional clinical tools for use at the point-of-care," Nanomedicine 5(1), 143-155 (2010).

Jokerst J.V., et al., "Programmable nano-bio-chip sensors: analytical meets clinical," Anal. Chem., 82(5), 1571-1579 (2010).

Jokerst, J.V., et al., "Nano-bio-chips for high performance multiplexed protein detection: determinations of cancer biomarkers in serum and saliva using quantum dot bioconjugate labels," Biosens Bioelectron. 24, 3622-3629 (2009).

Raamanathan, A., et al., "Programmable bio-nano-chip systems for serum CA125 quantification: toward ovarian cancer diagnostics at the point-of-care," Cancer Prev. Res. 5(5):706 (2012).

Rhodes, et al. Circle detection using a Gabor Annulus, 2011.

Rodriguez, W.R., et al., "A Microchip CD4 Counting Method for HIV Monitoring in Resource-Poor Settings," PloS Med. 2(7), 663-672 (2005).

Weigum, S. E., et al., "Nano-bio-chip sensor platform for examination of oral exfoliative cytology," Cancer Prev. Res. 3, 518 (2010).

Weigum, S.E., Floriano, P.N., Christodoulides, N., and McDevitt, J.T., "Cell-based sensor for analysis of EGFR biomarker expression in oral cancer," Lab Chip 7(8), 995-1003 (2007).

* cited by examiner

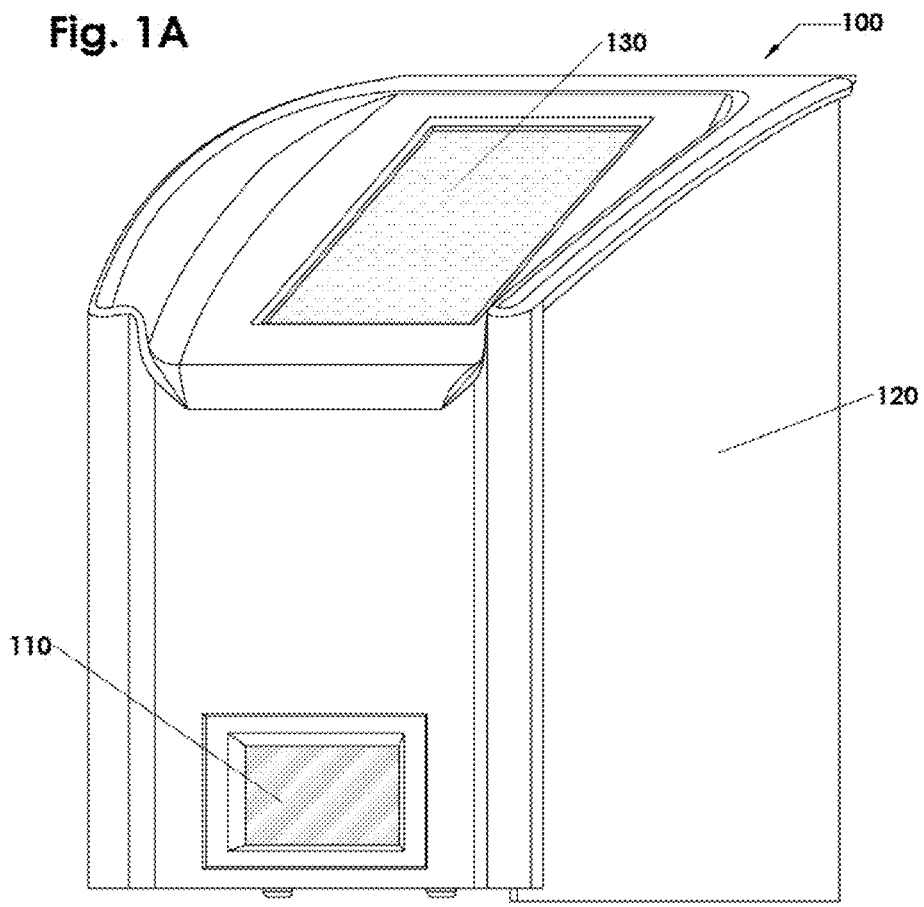

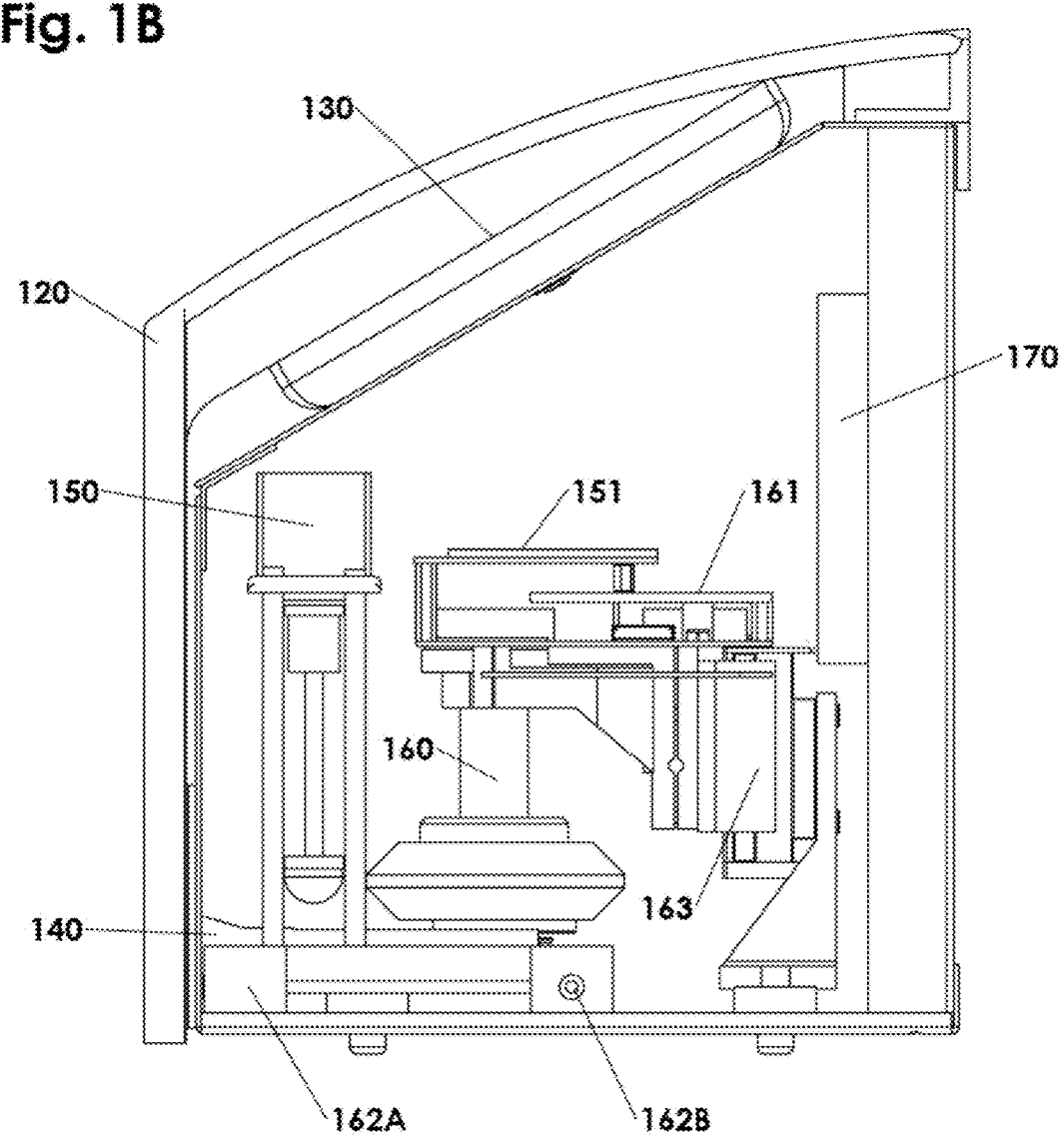

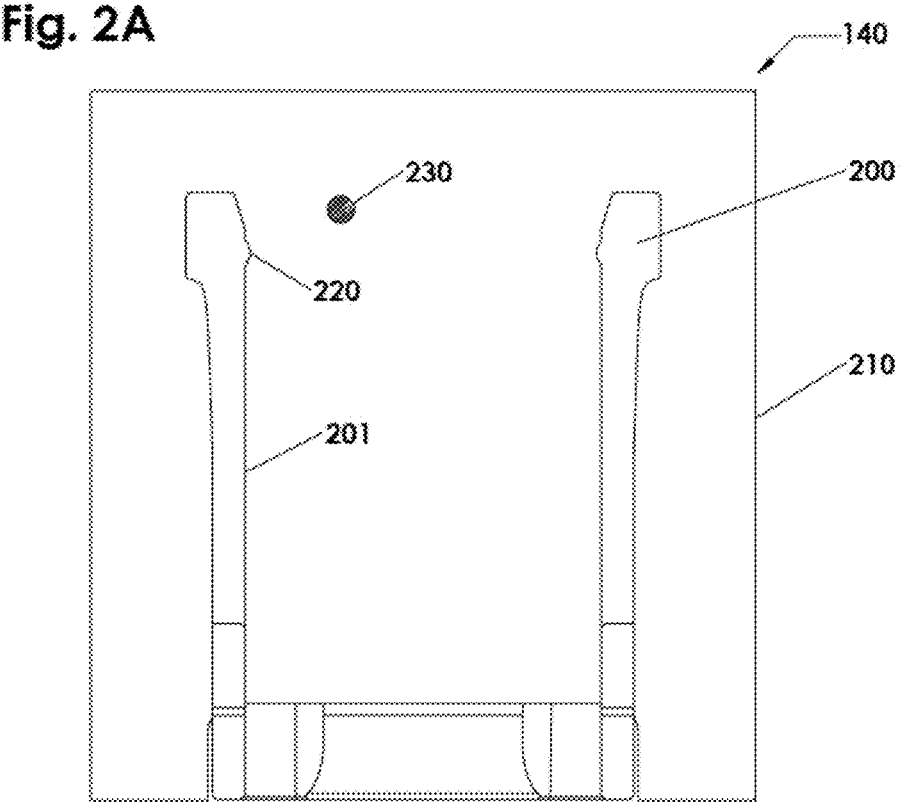
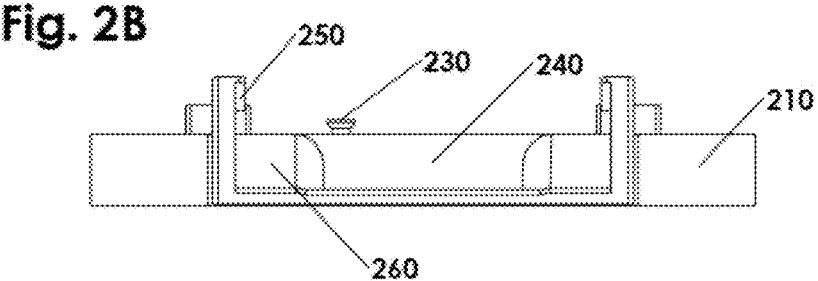

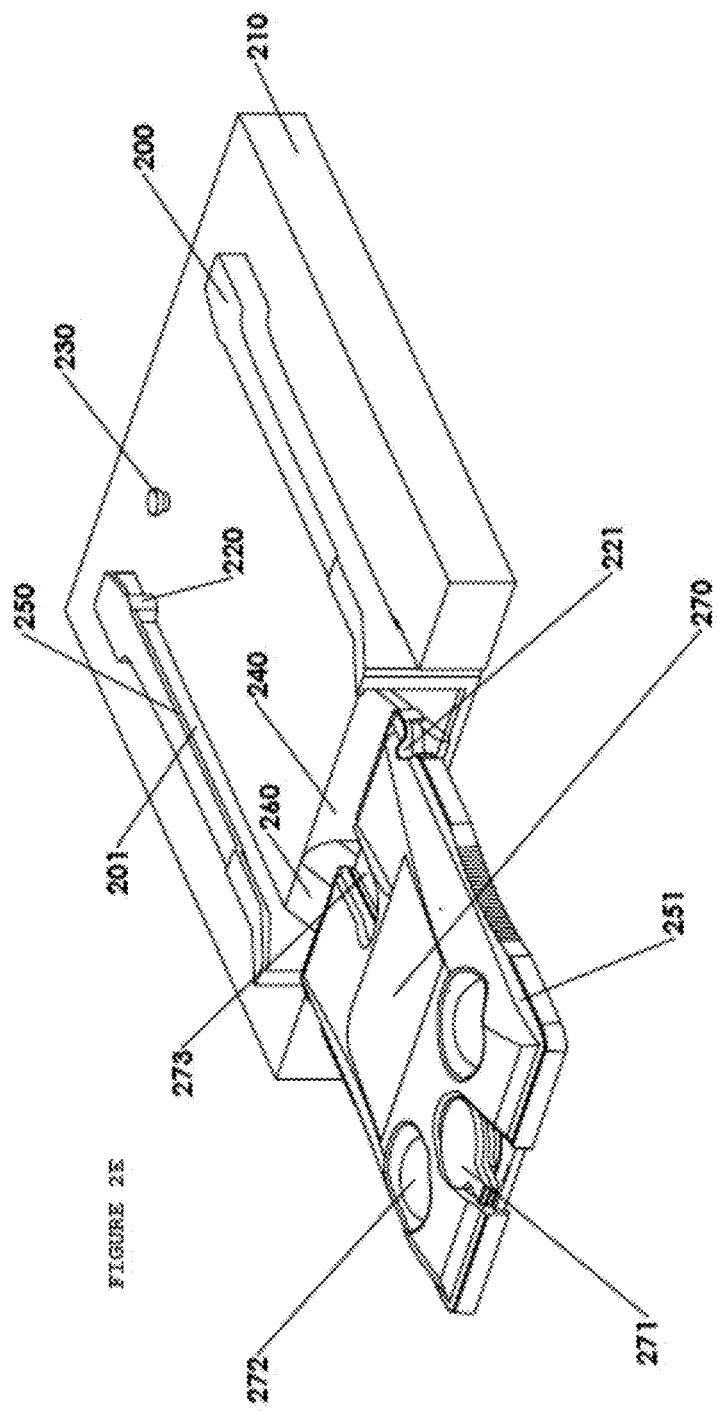

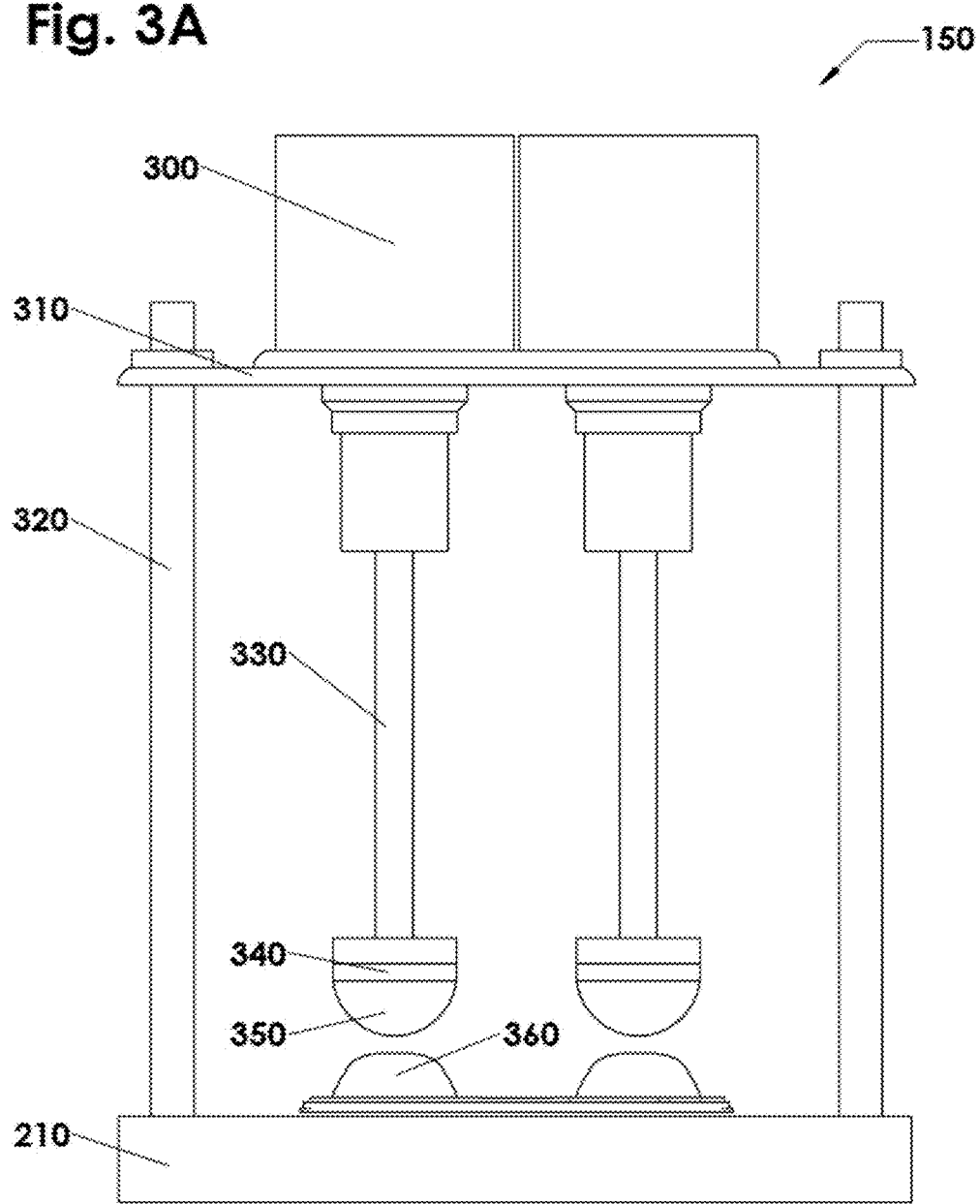

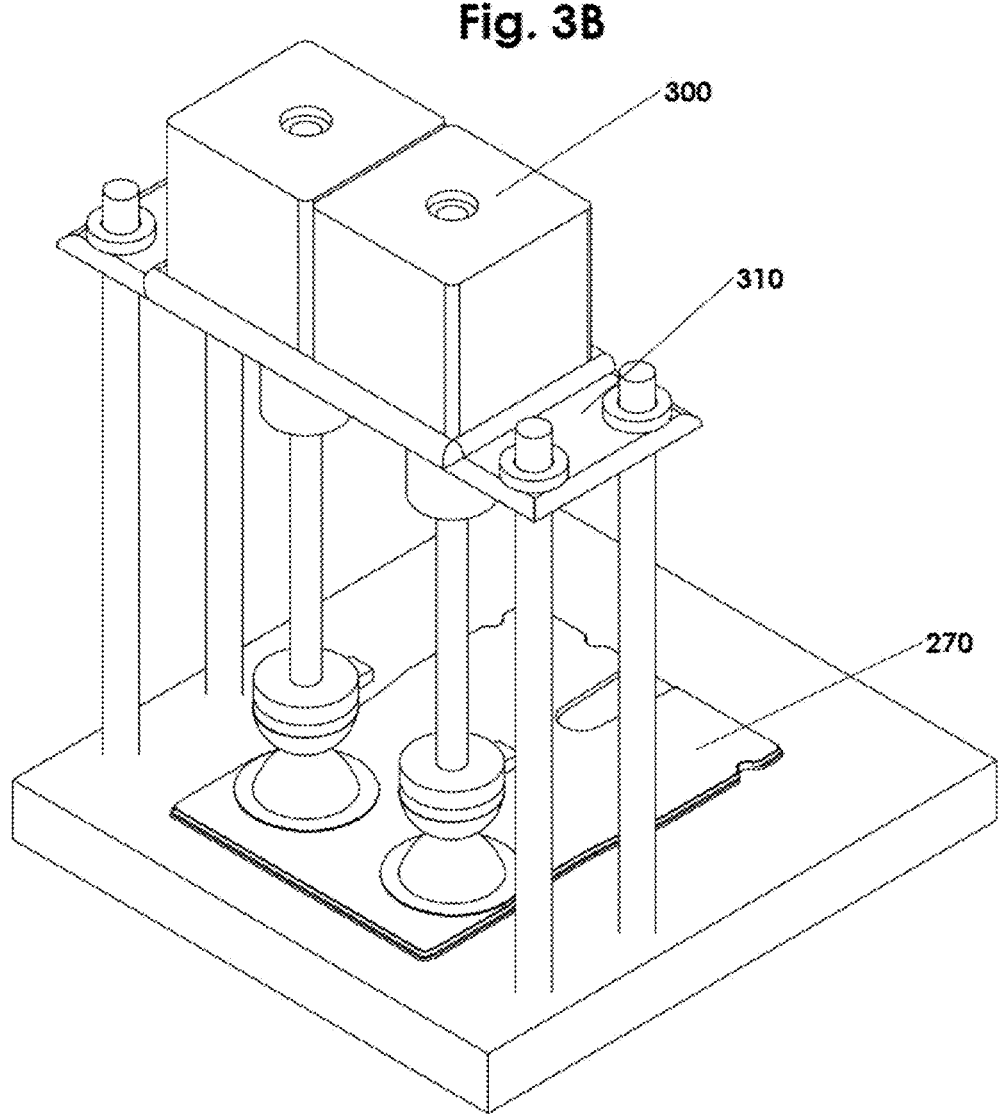

FIGURE 4
A
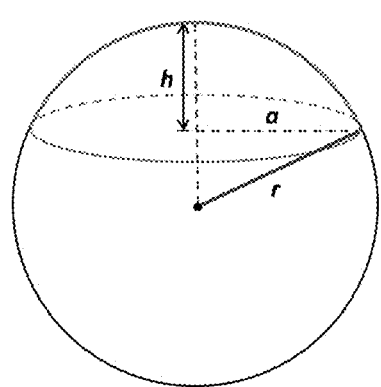
B
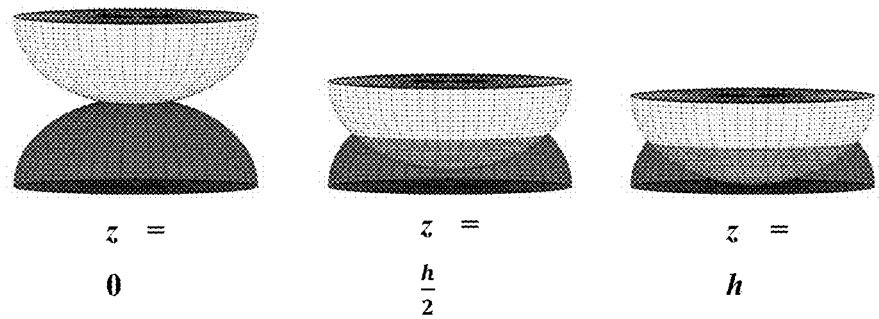
$z = 0$    $z = \frac{h}{2}$    $z = h$

INTEGRATED INSTRUMENTATION FOR THE ANALYSIS OF BIOFLUIDS AT THE POINT-OF-CARE

PRIOR RELATED APPLICATIONS

This invention claims priority to U.S. Ser. No. 61/841,090, filed Jun. 28, 2013 and incorporated by reference in its entirety for all purposes.

FEDERALLY SPONSORED RESEARCH STATEMENT

This invention was made with government support under Grant Numbers ARRA/NIH 1RC2-DE020785 and NIH 3RC2-DE020785-0251 awarded by the National Institute of Dental and Craniofacial Research (NIDCR) from the National Institutes of Health. The government has certain rights in the invention.

FIELD OF THE DISCLOSURE

The disclosure generally relates to portable instrumentation for point-of-care analysis. Specifically, an analysis hub, capable of analyzing various biomarker concentrations, serves as a portable reader and processor for biomarker assay cards.

BACKGROUND OF THE DISCLOSURE

In the last couple of decades, the use of biomarkers has become increasingly intrinsic to the practice of medicine and clinical decision-making Clinicians and researchers have rapidly been identifying biomarkers for clinical conditions ranging from heart disease and cancer, to Alzheimer's and dementia, to drug overdose and epilepsy. The number of published articles on biomarkers has increased substantially from under 200 in the early 1990s to well over 24,000 in the year 2011. This explosion in publication has meant that the last two decades have seen over 157,000 scientific publications.

This increasing interest in biomarkers is the result of their potential in heralding the much spoken of revolution in personalized medicine. However, biomarker testing has failed to be implemented in the clinical environment, and many different barriers prevent the complete utilization of biomarker testing.

First, only about 1 protein biomarker per year is approved by the Food and Drug Administration (FDA) for all diagnostic indications. Without regulatory approval, biomarker discoveries remain academic curiosities that simply do not impact patient care. The tools needed to facilitate the move of discoveries from validation into clinical implementation is lacking.

Second, the absence of a standard platform and pathway for approval has resulted in a 'biomarker bottleneck' that has prevented the highly anticipated revolution in personalized medicine from occurring.

Additionally, the lack of point-of-care analysis tools has limited biomarker based clinical decisions to far-off labs requiring delays between testing and treatment planning.

To address some of these issues, the McDevitt Research Group of Rice University (formerly of the University of Texas at Austin) has been developing and perfecting a novel bead based assay system called Programmable Bio-Nano-Chip and described in e.g. WO2012154306, WO2012065117, and WO2012065025.

Programmable Bio-Nano-Chip or "pBNC" utilizes microfluidics and advanced biochemistry to provide a rapid and easy-to-use method for obtaining quantitative biomarker assessments with potential use at the point-of-care, measuring various analyte species such as cells, proteins, small molecules, and DNA. "Programmable" describes the ability to chemically encode the pBNC to respond to different biomarkers. "Bio" refers to the capacity to isolate and quantify specific biomarkers from blood or saliva samples. "Nano" describes the scale of biomarker capture via nanonets. "Chip" refers to the potential for mass production of pBNC components. By utilizing the principles of microfluidics and a lab-on-a-chip approach, the pBNC assays provide a way for monitoring multiple biomarkers simultaneously, require drastically reduced volumes of chemical reagents, and can provide a biomarker diagnosis in minutes as compared to the week long-wait times of market available lab-based tests.

The bio-specimens and reagents are guided and delivered via a set of microfluidic pathways, etched into the lab card, onto the beads where the reaction takes place. Once the blood sample and reagents have arrived at the microbeads, a set of biochemical reactions take place which trigger the beads to fluoresce proportionally to the concentration of the biomarker of interest. Digital images of these beads can then be obtained using a simple laboratory-based fluorescence microscope, portable analyzer, or other optical devices and then processed by data analysis software to convert the fluorescent intensity into a biomarker concentration.

Despite significant advances in development of miniaturized sensing and analytical devices for use in clinical and biomedical applications, the ability to interface individual components to achieve high level of integration continues to pose a challenge for the lab-on-chip ("LOC") community. The heavy reliance on bulky pieces of equipment like syringe pumps, fluorescence microscopes, and infrastructure for analyzing the LOC devices can at times make such prototypes seem like chips-in-a-lab rather than true lab-on-chip devices.

Thus, with point-of-care applications, there is a need for a smaller system for performing biomarker analysis. Ideally, this system would act as a mobile analysis hub, capable of analyzing various biomarker concentrations.

SUMMARY OF THE DISCLOSURE

This disclosure relates to a system that can be utilized to perform analysis of biomarker assay cards. Specifically, the system is small and portable enough to facilitate point-of-care testing. Such a system finds use in both the lab and clinical settings. A method of using the system is also disclosed.

The novel aspect of the present invention is that it integrates the various components normally used in biomarker analysis in a single, portable system. This integration creates an analysis hub having a housing containing a slot for receiving an assay card, a processor having a user interface, stepper motors for compressing analyte- or reagent-filled blisters on the assay card, an optical or energy sensing means, and an optional means for storing supplies.

The processor and user interface control the system and the processor records data from said optical sensing means. Also preferred is a device that includes a display means operably connected to said processor for displaying said data, and a optional data-port that can connect to independent data storage and/or display means. Also preferred is a display capable of being activated by touch, i.e. a touchscreen.

The analyzer contains one or more of the following features, in any combination:

1. Universal analyzer—The universal analyzer serves as a platform that is capable of a broad range of biological and chemical testing, including soluble and cellular biomarkers. As such, the flexible instrumentation serves as a mechanism to digitize biology through the use of an imaging approach. Thus, the analyzer serves as a mechanical, software and user interface. The system serves as basis for eliminating the complex laboratory environment that more typically must be used to complete biomarker measurements. All sample processing, fluid routing manipulations, analyte separation, analyte quantitation, waste containment and result reporting steps are completed within the confines of the universal analyzer system.

2. Geometry of actuator footprint—The actuation of a dome-shaped blister was carried out by actuator footprints with many other geometric configurations. However, when the blister was actuated with a flat surface (as with the footprint in the LabNow analyzer), the interaction between the foot and the dome blister caused the blister to deform in an unpredictable way, often causing transient fluctuations in flow rate due to folding of the material on itself. Our solution uses a dome shaped actuator surface in order to obtain predictable and repeatable deformation of the blister.

3. Actuation rate adjusted for geometry—Another complication in accurately maintaining constant flow rate is that the geometry of the blister leads to flow rates that vary with actuation depth. As the actuator footprint compresses the blister, the contact surface area increases; thus, the flow rates increase as actuation into the blister progresses. We developed a mathematical model for actuation rate based on the interaction of two spherical caps. When applied to the blisters, the geometry adjusted actuation rate delivers a constant flow rate of reagents into the cartridge.

4. Force sensitive feedback for detecting blister location—The geometry adjusted flow rate works only when the location of the top of the blister is known. The blister actuator assembly contains a force sensitive resistor (FSR) that senses when the actuator makes contact with the top of the blister. The FSR also detects when the blister has been fully actuated by sensing contact with the base plate.

5. Force sensitive feedback for detecting blister bursting—The FSR assembly also detects when the blister has burst, and the actuator retracts to prevent reagents from rushing into the cartridge. Without the bursting feedback mechanism, the fast-moving fluid profile removes the beads from the wells.

6. Customizable flow protocols—The blister actuator module is capable of performing a variety of flow protocols that were previously not available on pre-existing analyzers (e.g., LabNow). This allows the pBNC analyzer to apply accurate flow rates between 1-200 µL/min to a wide variety of assays with various flow requirements.

7. Cartridge loading mechanism—The cartridge loading mechanism is a simple solution to mechanical stabilization. The alignment system contains no moving parts and leverages the elasticity and geometry of the guide rails to lock the cartridge's contours in place in the x, y, and z directions. The cartridge loading mechanism also allows the cartridge's sample loading port to protrude from the analyzer, preventing the cartridge from leaking from the sample port inside of the instrument.

8. Gabor annulus bead detection method—The Gabor annulus bead detection method replaces the pre-existing method of manually mapping the beads' coordinates. The Gabor annulus technique has been used to identify cells, but we believe it to be a new application for use in bead-based sensors. Previous methods involve manually entering bead edge coordinates in order to designate region of interest. The Gabor annulus method leverages computer vision to automate the process of locating beads. The novelty of our application lies in the use of multiple Gabor annulus filters aggregated in an ensemble to detect beads. By using filters with slightly different characteristics in an ensemble, we account for slight variations in bead sizes in our pBNC sensor.

9. Donut ROI pixel analysis—The donut ROI enhances the performance of the pBNC bead-based assay by localizing the region of interest to the edge of the bead where the signal develops. Instead of averaging the pixels of the entire bead (circle ROI method), the donut ROI method excludes pixels in the bead center and focuses on the pixels that form the signal around the edges of the bead. This method can be tuned to minimize intra-assay CV or maximize signal, allowing for lower limits of detection (defined here as 3 standard deviations above concentration zero measurement in a dose curve) or greater sensitivity, respectively.

10. Touchscreen interface—The touchscreen interface is a new feature that improves the user experience. The ability to connect to smart phones via mobile apps is also a new feature that allows the user to organize and track their health status.

Any commercially available optical module can be used, or the optical module can be manufactured specially for the present device. Commercially available optical imaging modules for microarray applications to date include the Sensovations™ LumSens, but we envision that a dedicated optical module will be manufactured to be specifically for this application, thus minimizing complexity of the device, while maximizing ease of use.

Any commercially available stepper motor can be used. Commercially available stepper motors include those from Sigma Instruments, Thorlabs, Haydon Kerk and the like. Any commercially available force sensor resistor can be used, and many suppliers including Tekscan, Trossen, Karlsson Robotics, and Adafruit, and the like exist. The FSR 400 series, Interlink Electronics were used herein, glued to the bottom-most contact surface of the actuator.

To facilitate portability of the system, the entire system is small—roughly 5-10 inches×6-12 inches×5-10 inches, such that it can be carried or fit on a rolling cart and thus easily transported.

The system may also be connected to a computer and display such as a fully operating PC for data processing and display, a micro Bluetooth adapter dongle for wireless communication to smartphone devices, and other external devices. Additionally, accessory holders for syringes and clinical tools can be included on the device.

The methods, devices, and systems include any one or more of the following embodiments, in any combination;

An analyzer for a lab card, said analyzer comprising:
an optical imaging module located above a sample platform;
one or more blister actuators located above said sample platform, each blister actuator having a stepper motor for moving said blister actuator up and down and a force sensor resistor for detecting a force on said blister actuator;
a processor operably connected to said optical imaging module and to said blister actuator, wherein said processor controls and collects data from said optical imaging module, and controls said blister actuator;
each of components a-c housed inside a housing;
said housing further comprising a lab card slot in communication with said sample platform and a user interface, wherein the user interface is in communication with said processor.
An analyzer wherein said housing further comprises a connector for cables connecting said processor to external display or storage devices.
An analyzer wherein said optical imaging module detects fluorescence light signals from a lab card.
A system said optical imaging module comprising a microscope, a light source, and a photodetector for detecting light from a lab card.
An analyzer, said optical imaging module comprising a microscope, a light source, one or more optical filters, and a photodetector for detecting light from a lab card.
An analyzer said optical imaging module an LED light source, and a CCD or CMOS camera for detecting fluorescence from a lab card.
An analyzer wherein said housing is lightproof when a lab card is inserted into said lab card slot such that external light does not reach said optical imaging module.
An analyzer wherein said external housing further houses a supply storage container.
An analyzer wherein said processor accommodates a geometry of a blister on a lab card to adjust a rate of movement of said blister actuator to deliver a constant flow rate of a fluid from said blister.
An analyzer wherein said force sensor resistor detects the top of said blister upon actuation by said blister actuator and detects a controlled burst of the blister and subsequent release of reagents into a lab card
An analyzer wherein said blister actuator movement slows with increasing compression of a rounded blister.
An analyzer wherein said blister actuator is semispherical and its movement slows with increasing compression of a semispherical blister.
An analyzer wherein said blister actuator is semispherical and its movement slows with increasing compression of a semispherical blister according to equation A and B:

$$Q = \frac{dV}{dz}\frac{dz}{dt} \qquad \text{Eq. A}$$

where Q is the desired flow rate, $\frac{dz}{dt}$ is the actuation rate, and $$\frac{dV}{dz} = \frac{(3r - \frac{z}{2})\pi z}{3} - \frac{\pi z^2}{12} \qquad \text{Eq. B}$$

where z is the actuation depth, and r is the radius of said semispherical blister and V is the volume of the blister.
An analyzer wherein said processor utilizes Gabor annulus method for automatically locating bead region of interest in a lab card.
An analyzer wherein said processor averages the normalized results from two, three, or multiple Gabor annulus convolutions to improve accuracy of bead location.
An analyzer wherein said processor utilizes donut region of interest analysis for detection of signals present on a bead in a lab card, and exclude signals from a center of said bead.
An analyzer wherein said processor utilizes donut region of interest analysis to optimize the radius of interest for minimum intra-assay CV or maximum signal intensity
An analyzer wherein said processor utilizes donut region of interest analysis for detection of signals present on a bead on a lab card, and exclude signals from a center of said bead.
An analyzer wherein said processor averages the normalized results from two, three, or multiple Gabor annulus convolutions to improve accuracy of bead location and utilizes donut region of interest analysis to optimize the radius of interest for minimum intra-assay CV or maximum signal intensity.
A system including the analyzer herein described and any lab card, preferably the pBNC described by McDevitt's group.
A system including the analyzer herein described herein and any lab card plus external components including any one or more of a power source, fluid source(s), pump(s), sample dispensers, sample handling robotics, and the like.
A method of analyzing a lab card, comprising the steps of:
inserting a lab card having rounded blisters into a card slot located on an external housing, wherein said card slot is in communication with a sample platform, wherein said inserted lab card rests on said sample platform;
compressing said rounded blisters located on said biomarker assay card using a blister actuator and stepper motors within said external housing to move said blister actuator vertically, wherein said blister actuator slows said blister actuation with increasing compression;
wherein said compressed blisters release reagents and/or analytes into said lab card;
obtaining optical images of said lab card using an optical imaging module located above said lab card;

-continued processing said optical images on a processor located within said external housing to obtain an assay result; and
displaying said assay result on a display means connected to said processor.
A method said lab card including a bead conjugated to an antibody.
A method wherein said processing includes Gabor annulus bead detection for automated location of beads by said processor.
A method wherein said processing includes donut region of interest processing of signal from said bead, ignoring signals from a center of said bead.
A method wherein said processor averages the normalized results from two, three, or multiple Gabor annulus convolutions to improve accuracy of bead location and utilizes donut region of interest analysis to optimize the radius of interest for minimum intra-assay CV or maximum signal intensity.
A method wherein said compressing step b further comprises lowering blister actuator until a force sensor resister detects contact with said blister,
A method wherein said processor communicates with said force sensor resistor and said blister actuator while the blister actuator moves vertically toward said blister, wherein the processor recognizes when the blister actuator makes contact with the blister via a signal from the force sensor reaching a voltage threshold.
A method wherein said processor communicates with said force sensor resistor and said blister actuator while the blister actuator compresses said blister and stops the blister actuator upon bursting the blister when the signal from the force sensor exhibits a change in voltage signal from sudden pressure release of blister contents into said lab card.

As used herein, the term "analyzer" refers to the portable system herein described that functions to perform assays on a lab card, analyze and display results.

As used herein, the term "lab card" or "assay card" refers to a customized cartridge for a particular reaction type that houses microfluidics and reagents to perform one or more chemical or biological assays. The analyzer described herein is exemplified with a lab card containing two reagent blisters and one or more reaction wells, each housing one or more agarose beads to which target specific reagents (such as antibodies) are bound, but the lab card design and function can vary according to the needs of the reaction of interest.

As used herein, "blister actuator" is a device that moves up and down in order to compress a fluid containing blister on a lab card, in order to deliver fluid to the reaction wells at the appropriate time. We have described semispherical blisters and actuator heads herein, but other geometries can be realized using the principles described herein.

As used herein a "blister" is a watertight, fluid filled container on a lab card that is intended to be activated by compression and/or piercing, forcing fluid from the blister into the microfluidic pathways of the lab card and thus into the reaction wells. Typically, blisters are made of foil, but other waterproof films could be used.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
| --- | --- |
| AMI | Acute myocardial infraction |
| CAD | Coronary artery disease |
| CCD | Charge coupled device |
| COC | Cyclo olefin copolymer |
| CMOS | Complementary metal-oxide-semiconductor |
| cTnI | Cardiac troponin I |
| DSA | Double-sided adhesive |
| FSR | Force sensitive resistor |
| IVD | In vitro diagnostic |
| LED | Light-emitting diode |
| LOC | Lab-on-a-chip |
| pBNC | Programmable Bio-nano-chip |
| PC | Polycarbonate |
| PET | Polyethylene terephthalate |
| POC | Point-of-care |
| USB | Universal Serial Bus |

BRIEF DESCRIPTION OF THE DRAWINGS

FIG. 1A shows the exterior of the portable analyzer for a lab card.
FIG. 1B shows an interior side view of the analyzer's interior (cover removed).
FIG. 2A shows a top view of the precision cartridge alignment system.
FIG. 2B shows a front view of the precision cartridge alignment system.
FIG. 2E shows the cartridge alignment system 140 and lab card 270 in perspective.
FIG. 3A shows a side view of the automated fluid delivery system.
FIG. 3B show a perspective the automated fluid delivery system.
FIG. 4 shows the blister actuation model. A) Spherical cap geometry used in the construction and modeling of blister and actuator interactions, B) 3D representation of blister (blue) and actuator footprint (white) interactions
FIG. 5. Flow verification results showing flow rate vs. normalized actuator position (from blister top to bottom).

DETAILED DESCRIPTION

Figure 2C:
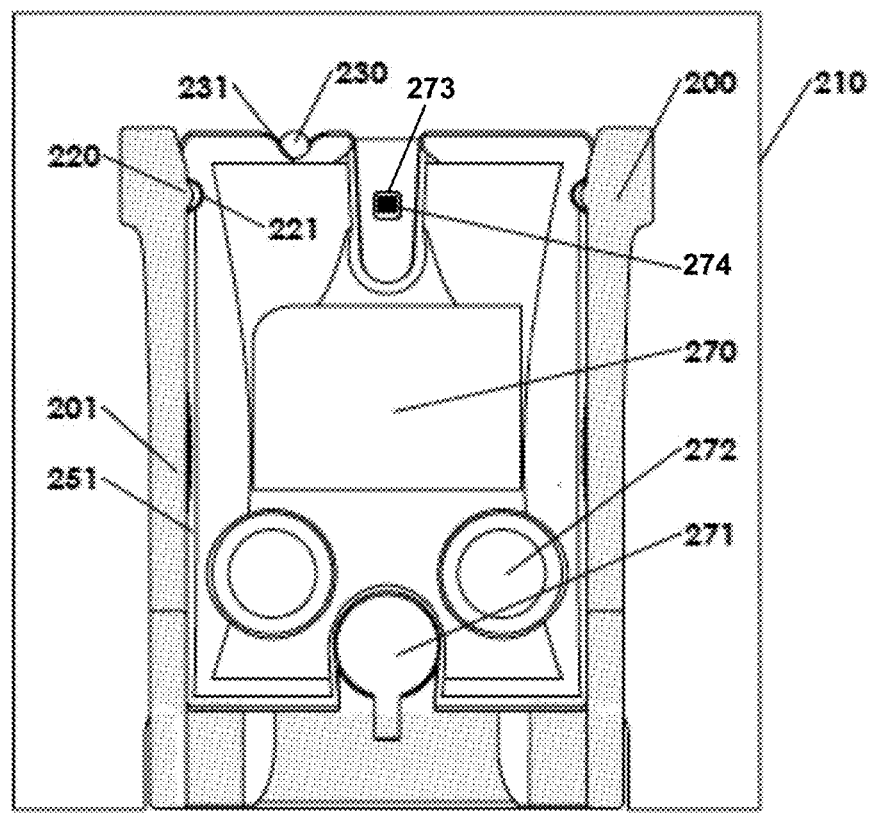
FIG. 2C shows a top view of the same precision cartridge alignment system with the lab card fully inserted.

The pBNC system consists of two main components: the disposable cartridge or lab card and the portable analyzer. The invention of the disposable cartridge is addressed in separate applications, while this patent application focuses on the integrated instrumentation that comprises the pBNC analyzer.

The pBNC analyzer is a new device that performs assays in a fully automated fashion to yield highly reproducible, accurate, and precise measurements in a research, clinical, or point-of-care (POC) setting.

The portable pBNC analyzer performs assays on the pBNC disposable cartridges and is specifically designed to interface with the pBNC cartridges, although other lab cards can be used with the analyzer, provided they meet the various geometry requirements. The pBNC disposable cartridge is self-contained, integrated, and has reagents conveniently embedded for ease of use at POC. The bio-specimen (whole blood, serum, or saliva) is introduced into the sample loading port on the cartridge. A conjugate pad with dried reagents (e.g., detecting antibody) may be embedded in the lab card and dissolved as needed through the activation of buffer-containing blister-packs. The bead-based lab card contains analyte-specific antibodies bound to agarose beads supported in a plastic microchip. The mini-sensor ensemble is capable of multiplexing fluorescence immunoassays for proteins, oligonucleotides, and small molecules. This system replaces the gold-standard method, enzyme-linked immunoassay (ELISA), in terms of analysis time, limits of detection, and ease-of-use.

The analyzer for the pBNC cartridge consists of precision cartridge alignment, automated fluid delivery, miniature fluorescence optics module, touchscreen interface, embedded PC, and protective enclosure (FIG. 1). The current prototype analyzer is already being used to analyze clinical samples in the lab, but future iterations of this analyzer are envisioned for deployment into research, clinical, and POC areas.

Analyzer

In more detail, FIG. 1A shows the exterior of the portable analyzer 100 for the pBNC. The analyzer 100 exterior consists of a cartridge slot 110 for inserting the pBNC cartridge, protective enclosure or housing 120, and touchscreen interface 130. The protective enclosure integrates major elements of the instrument into a unified configuration that blocks light from the optics module and protects the internal components from dust, liquid and light.

The exterior of the pBNC instrument supports, encloses, and protects the instrumentation modules from the environment. Arrangement of PC, motor- and optics control boards prevent cartridge or blister leaks from damaging the hardware. The protective enclosure or housing of the prototype model included the following:

Protects the internal components from the environment
Prevents stray light from fouling data acquisition
Supports the touchpad user interface
Has USB fan and vents for cooling
Contains back panel with electronic interfaces for the following
DB-15 connector for powering Sensovation LumiSens
DC input for powering embedded PC
3 USB A-A connectors
RJ45 In Line Adapter for internet connection
HDMI for projecting screen to external monitor The analyzer's interior is shown from the right side in FIG. 1B where part of the protective enclosure 120 was omitted to show internal components. The major components of the analyzer are precision cartridge alignment 140, automated fluid delivery system 150, optics module 160, touchscreen interface 130, embedded PC 170, and protective enclosure 120.

Also shown are the optics control circuit board 161 for controlling the image capture hardware and motor control circuit board 151 which controls the automated fluid delivery system 150, the z-axis focus actuator 163 for focusing the optics, and the x- and y-axis linear actuators 162A and 162B for translating the cartridge stage in x and y directions. The embedded PC 170 and software controls all components through USB communication with optics controller board 161, motor controller board 151, and touchscreen interface 130.

The prototype analyzer contains a mini-PC and touchscreen with the following features:

GIGABYTE GB-BXi3-4010 Barebone Mini-PC
Intel Core i3-4010U 1.7 GHz
Intel HD Graphics 4400 Integrated by CPU
2x 204 Pin
Supports DDR3L (low voltage 1.35 memory)
Windows 7
Mimo 720S Touchscreen Monitor
7 inch screen monitor
800 × 480 resolution LCD
High speed USB 2.0 powered/interfaced The touchscreen interface is the main method of interacting with the portable analyzer; however, the analyzer may be tethered to an external PC via USB for controlling major components, and the touchscreen display may be extended to an external monitor via HDMI. Although the embedded PC in the analyzer is Wi-Fi enabled, the back panel includes an Ethernet cable (Cat 5e) for wired internet connectivity.

Cartridge Alignment

The cartridge loading mechanism was designed for two purposes: 1) to stabilize the cartridge in x, y, and z directions with the bead array centered under the optics field of view; 2) to allow easy insertion and removal of the disposable cartridge by a non-expert user.

The 3D printed plastic cartridge loading mechanism has a wide mouth that accepts the cartridge and channels it into the proper alignment. When partially inserted, the cartridge is stabilized on top, bottom, and on both sides by the guide rails, and it glides easily into position, where matched protrusions and depressions ensure a snap fit insertion, preventing over or under insertion.

The cartridge has three alignment features on its outer shell to facilitate mechanical stabilization: two on both sides and one in the upper left corner (when cartridge lays flat). When the cartridge is fully inserted, positive features that coincide with the side alignment features bend outward and then lock the cartridge into place (e.g., cantilever snap fit guide rails). A mechanical stop interacts with the alignment feature on the upper left corner of the cartridge for additional stabilization of the cartridge and to prevent the user from over-inserting or under-inserting the cartridge.

In more detail, FIG. 2A (top view) and FIG. 2B (front view) show the precision cartridge alignment system 140 that is accessed through the cartridge slot 110 on the exterior of the analyzer. The cartridge loading mechanism 200 is anchored to an acrylic stage 210, which supports the bottom of the cartridge. The alignment system contains the cartridge loading mechanism 200 which stabilizes the cartridge in x and y directions via two guide rails 201 on either side of the cartridge, allowing easy insertion and removal of the cartridge by a non-expert user. The guide rails can be deflected a certain amount on lab card insertion, snap fitting back into place when the protrusions 220 meet the corresponding depressions 221 in the lab card. Thus, the guide rails provide a cantilevered snap fit for the lab card.

A cartridge guiding ramp 260 allows the precision cartridge alignment system to accept cartridges from multiple insertion angles. A void 240 space in the guiding ramp 260 allows the user to reach deeper into the instrument with his/her fingers to insert or remove the cartridge.

Figure 2D:
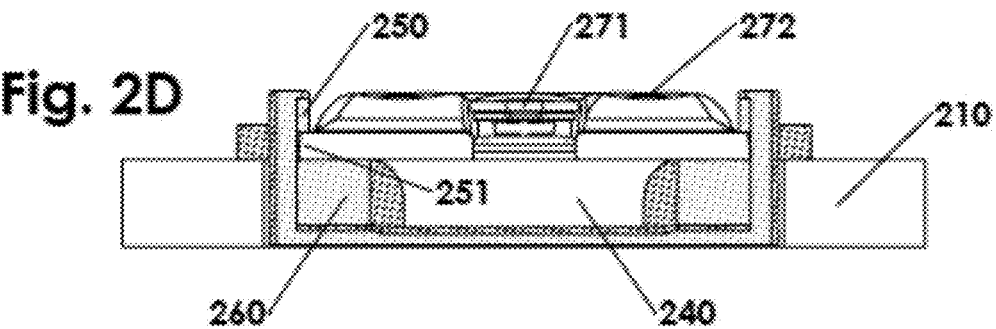
FIG. 2D shows a side view of the same precision cartridge alignment system 140 with the pBNC cartridge 270 fully inserted.

FIG. 2C and FIG. 2D show the same precision cartridge alignment system 140 with the cartridge 270 fully inserted. Sample inlet 271 and paired blisters 272 are seen that line up with the blister actuators (not seen in this figure, but see actuator feet 350 in FIG. 3A). The reaction well 273 with bead array 274 (black) is also seen, but the internal microfluidics are not visible.

Positive alignment features 220 (protrusions) on the cartridge alignment guide rails 201 interact with complementary features (depressions) on the cartridge 221. The guide rails also have an overhanging protrusion or ledge 250 that holds the flat portion of the cartridge shell 251 down in the z direction. The cartridge alignment system precisely aligns the cartridge with blister actuators, LED illumination, and optics field of view (tolerance of <0.1505 mm in x and y directions). A precision pin 230 is also fixed to the stage 210, which interacts with an alignment feature (notch or depression) on the cartridge 231 and performs two functions: aligns the cartridge under the and the blister actuators and prevents the user from over-inserting the cartridge.

FIG. 2E shows the cartridge alignment system 140 and lab card 270 in perspective, more clearly showing the guiding ramp 260 and full width void 240 under the lab card 270, which aids in removal by providing a finger insertion space. On lab card 270 insertion, the card 270 slides up ramp 260, is caught under ledge 250, pushing guide rails 201 aside slightly. Insertion continues until pin 230 meets notch 231 and protrusion 220 meets depression 221, thus allowing guide rails 201 to snap fit back into position.

Geometry-Adjusted Blister Actuation Rate

The analyzer is programmed to run an extensive menu of assays on the lab cartridge with various flow protocols. FIG. 3A and FIG. 3B show the automated fluid delivery system 150 in more detail. The analyzer delivers fluid into the microfluidics of the cartridge by compressing the blister packs 272 mounted directly on the lab cartridge 270. Two linear actuators 300 are fixed to an actuator support structure 310 such that the actuators are centered over the cartridge's blisters 272. Obviously, the actual number of actuators should either reflect the number of blisters, or movement means must be provided to move the actuator to the next blister.

The actuator support structure 310 is held by four carriage bolts 320 fastened to the cartridge stage 210, but other attachment means could be used. Actuator shaft extenders 330 allow the actuators to be mounted such that they avoid interacting with the optics module. Force sensitive resistors 340 are affixed to the bottom of the actuator extenders 330 (between the extenders 330 and feet 350) and allow pressure sensitive feedback for sensing blister interactions. The dome-shaped actuator feet 350 compress the blisters 360 and are described in detail next.

One complication in maintaining constant flow rate is that the geometry of the blister leads to flow rates that vary with actuation depth. As the actuator compresses the blister, the contact surface area increases; thus, the flow rate increases as actuation into the blister progresses. Careful manipulation of the actuation rate can counteract flow rate variation that arises from the blisters' spherical cap geometry and deliver the desired constant flow rates for the biochemical assay.

Blister actuation for the analyzer was first modeled as two identical spherical caps corresponding to the blister and the actuator footprint, however, the blister and actuator footprint may be of slightly different geometries (e.g., in FIG. 3A) and obtain adequate results. Using a thermoforming fabrication process, blisters and actuator feet were made from the same mold. The total volume of the blister is given by the volume of the spherical cap in Eq. 1.

$$V = \frac{\pi h^2}{3}(3r - h) \qquad \text{Eq. 1}$$

Here, r is the radius of the sphere and h is the height of the spherical cap. The total blister volume is the total volume capacity of the blister; however, after actuation there is residual fluid due to the interaction between the bottom of the blister and the actuator footprint. To determine the total ejection volume (volume of the blister minus residual volume) as a function of actuation depth the interaction of two spherical caps is modeled. The actuation depth, z, is given by the apex of the actuator footprint from the top of the blister (z=0) to the bottom of the blister (z=h). Since the spherical caps have identical geometry, the volume ejected at actuation distance z is simply the volume of two spherical caps at depth $$\frac{z}{2}.$$

using Eq. 1 and writing h in terms of $$\frac{z}{2},$$

$$V(z) = \frac{2\pi}{3}\left(\frac{z}{2}\right)^2\left(3r - \frac{z}{2}\right). \qquad \text{Eq. 2}$$

FIG. 4 shows the blister actuation model. A) Spherical cap geometry used in the construction and modeling of blister and actuator interactions, B) 3D representation of blister (blue) and actuator footprint (white) interactions.

The volume ejected per step of the linear actuator is needed to adjust the flow rate as a function of actuation depth. Deriving V in terms of z from Eq. 2, $$\frac{dV}{dz} = \frac{(3r - \frac{z}{2})\pi z}{3} - \frac{\pi z^2}{12}. \quad \text{Eq. 3}$$

The volumetric flow rate is then given by $$Q = \frac{dV}{dz}\frac{dz}{dt}. \quad \text{Eq. 4}$$

The desired constant flow rate Q is generated by applying the actuation rate $$\frac{dz}{dt}.$$

To generate constant flow of reagents, the stepper motor driver sends alternating high and low voltage signals to the motor in a synchronized fashion such that the time delay instructions to the linear actuators scale with the volume ejected as actuation depth into the blister increases. The blister actuator device is currently controlled by a graphical user interface (GUI) developed in MATLAB (not shown).

The prototype blister actuator module contained the following:

Two captive linear actuators
Size 14 Series 35000, Haydon Kerk
3D-printed plastic support structure for actuators
Fastened to a 12.7 mm thick acrylic base with a 101.6 × 25.4 mm perimeter via four threaded carriage bolts
Motor controller board operates the stepper motor drivers
Two stepper drivers (EasyDriver, Schmalz Haus LLC)
180 ± 20 mA per phase using chopper microstepping driver
Allegro A3967 driver chip (8 step microstepping mode)
Linear travel at 0.38 µm per step
Arduino Pro Mini (5 V/16 MHz)
ATmega328 chip
USB/A to serial converter (FTDI cable, 5 V)
Pressure sensitive feedback for sensing blister burst, initiates start of assay sequence
Force sensitive resistors (FSR 400 series, Interlink Electronics) attached to the bases of the actuator extenders
Actuator feet directly interact with the blisters
Cast in optically clear epoxy (Norland Optical Adhesive 81) from molds identical to the dome-shaped blisters
Bonded to the surface of the force sensitive resistors Flow rate verification of our geometry controlled blister actuation was performed using video analysis to track the flow profile of dyes through a specially designed microfluidic structure during blister actuation. An automated video analysis tool was created to assist the data acquisition process. Videos were recorded at 30 fps. The video analysis tool captures the location of the leading edge flow profile every 1 second.

Figure 5:
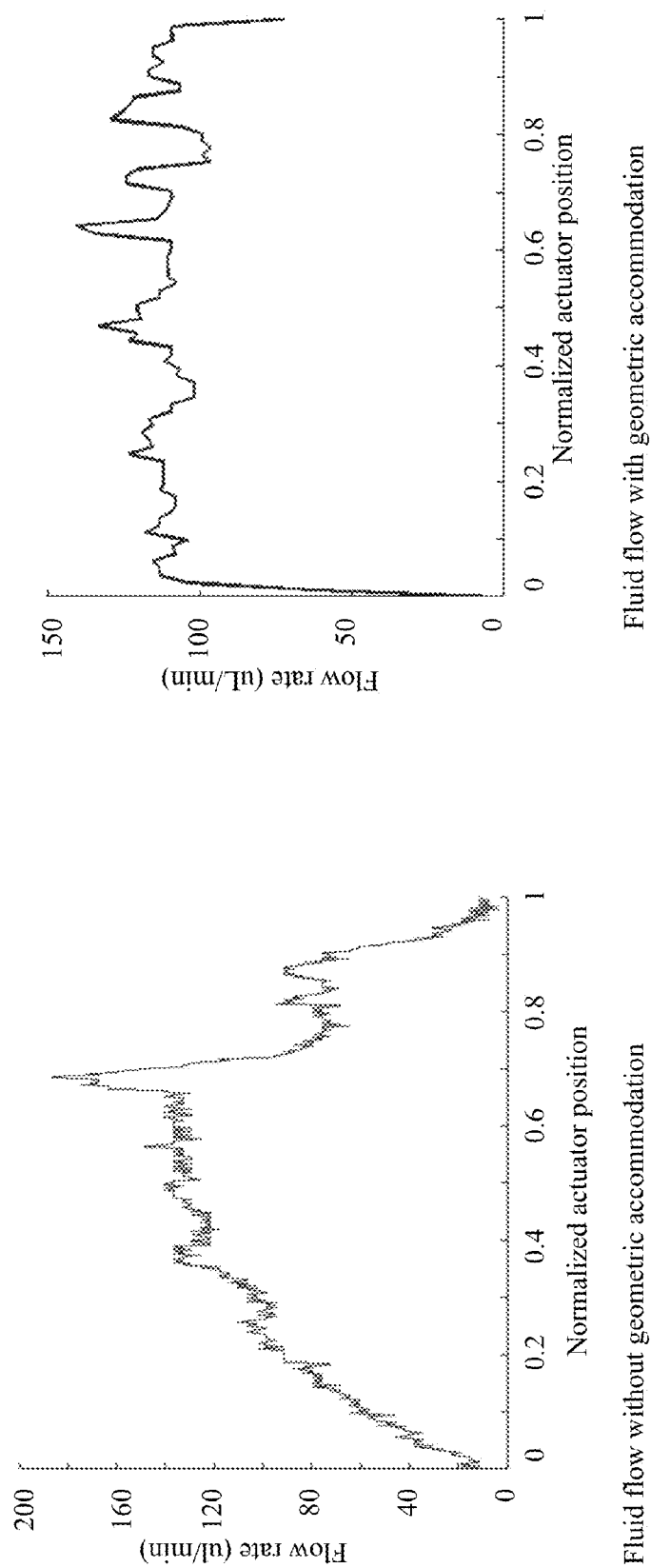

FIG. 5 shows data collected using constant actuation speed and geometry-adjusted actuation rate. Geometry-adjusted actuation (right) yields a constant flow rate around the target 100 µL/min. Unadjusted actuation (left) yields a flow rate that increases with actuation depth. The current experimental fluidic structures contain long meandering channels. For simplicity, the flow profiles around the bends of these channels were neglected. These preliminary results suggest that the actuation rate utilizing our mathematical description of spherical cap geometry leads to more constant flow rate around the target (100 µL/min).

Imaging Module

Figure 6A:
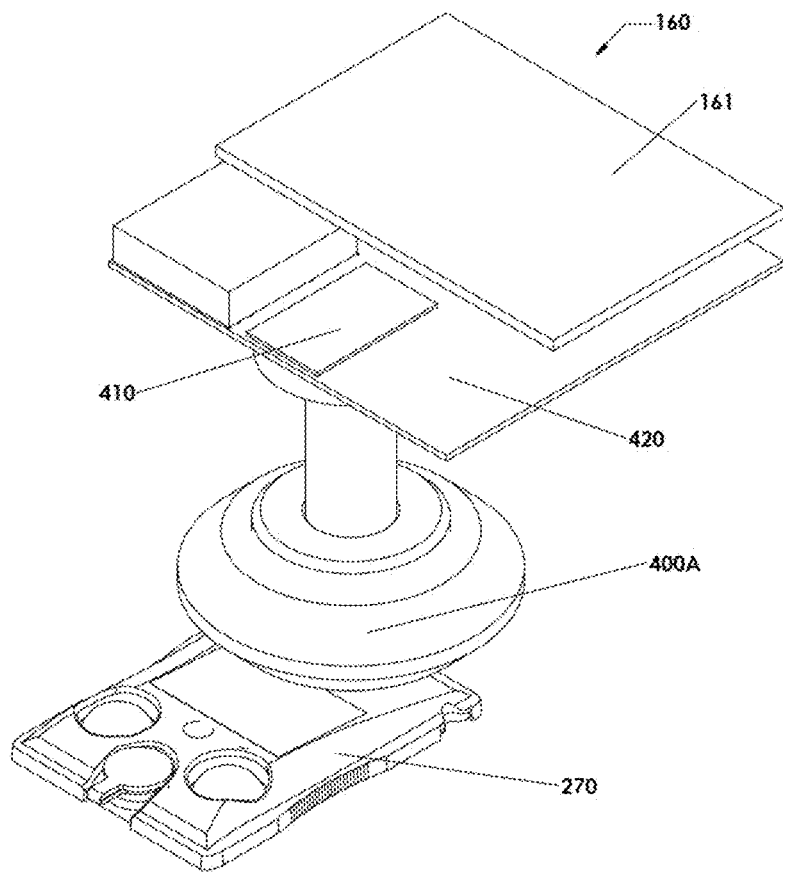
FIG. 6A shows a perspective of the optics module and pBNC cartridge.

FIG. 6A shows the optics module 160 and pBNC cartridge 270. The optics module is a miniature fluorescence microscope composed of a ring of LEDs 400A that encircles the objective lens and obliquely illuminates the bead sensors using two-color fluorescence (Alexa Fluor 488 and 647) and one reflected color for bright field. The objective lens 430 is encircled by LED ring 400A and has field of view 4 mm in diameter and 4.3× magnification with numerical aperture 0.3. A CCD 410 mounted to the camera board 420 captures images of the bead sensors. Images are 12-bit resolution captured by the graphical user interface. The images are transmitted to the embedded PC via USB communication with optics controller board 161.

Figure 6B:
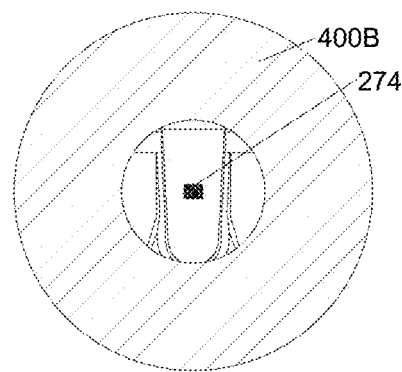
FIG. 6B shows the pBNC's bead array through the LED ring as seen by the objective lens.

FIG. 6B shows the pBNC's bead array 274 through the LED ring 400B as seen by the objective lens.

The pBNC optics module for the prototype—LumiSens—is a miniaturized fluorescence imaging system designed and fabricated by Sensovation. In summary, the LumiSens features:

Two color fluorescence (Alexa 488 and Alexa 647), and one reflected color for bright-field
Application for cell imaging and bead based biochip arrays
High quality consumer grade CCD (Kodak full frame 8300, KAF-8300-AXC-CD-AA)
Objective lens
Field of view 4 mm in diameter
4.3X magnification
NA 0.3
12 bit resolution images (.tif)
Sensovation graphical user interface
Illumination via ring of obliquely oriented, high power LEDs
5 VDC (6 A) powered by type B electrical outlet to regulated DB15 connector
6 A at operating voltage 5 VDC
Optics controller - USB/B terminal for serial communication between PC and camera
Camera board - contains the Kodak full frame 8300 CCD and directly interfaces with the objective lens Automated Image Analysis The analyses of raw images recorded from the pBNC analyzer CCD are performed automatically by the embedded PC using the pBNC's image analysis software developed in the McDevitt lab. Recent efforts towards automated image analysis for the pBNC have produced a functional software prototype with good agreement with performance of analogous manual methods. The prototype software consists of a novel methods for detecting the location of beads using a Gabor annulus approach and analyzing pixels according to various regional and intensity-based parameters, such as the donut region of interest (ROI) method. The following sections describe recent developments towards complete automation of image analysis.

The Gabor annulus method described by Rhodes et al. (13) is based on the advantageous properties of Gabor wavelet filters. Gabor wavelet filters are a popular method in computer vision for recognizing patterns. In this method, the radial symmetry of circular image features is exploited. The detection of bead edges in an image becomes difficult when there is image noise, imperfect symmetry, or fluorescent artifacts in the bead. The filter is defined by $$G(x, y) = \frac{1}{2\pi\sigma r_0} e^{-\pi\left[\frac{(r-r_0)^2}{\sigma^2}\right]} e^{i[2\pi f_0(r-r_0)]}$$

where $$r = \sqrt{(x-x_0)^2 + (y-y_0)^2}$$

This filter is applied to an image via convolution. The result is a maximum response in areas where an image containing features or patterns match their specific scale, orientation, and location. In other words, the filters may be fine-tuned recognizing the characteristics of beads, and the result of applying the Gabor annulus filter is the location of the bead center.

Figure 7:
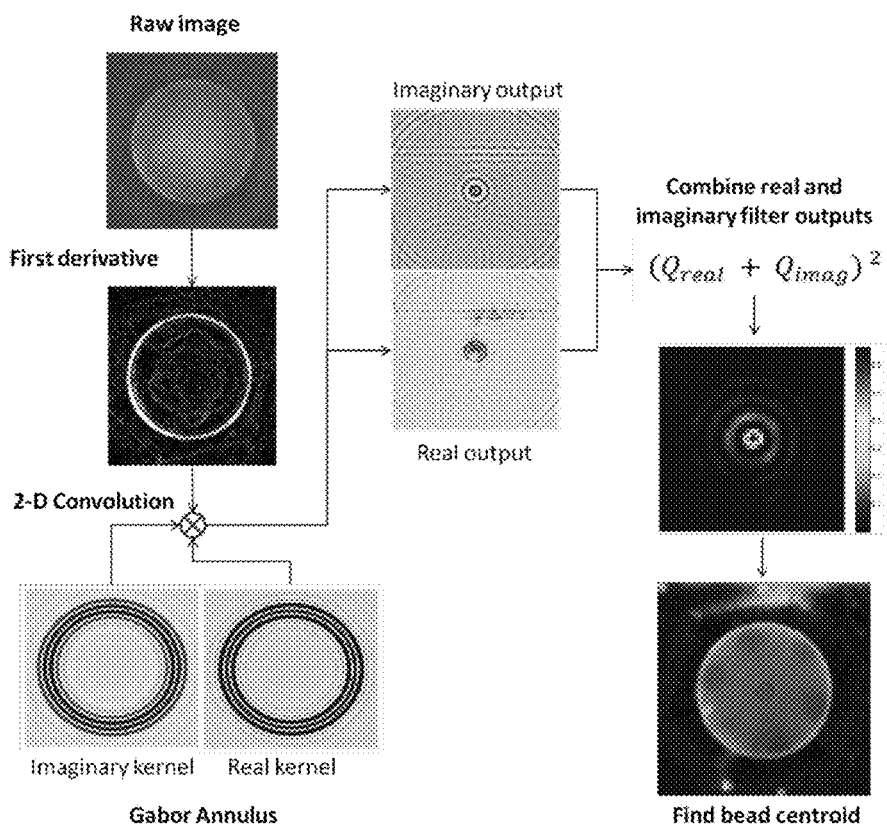
FIG. 7 demonstrates the Gabor annulus method of bead detection.

FIG. 7 illustrates the basic process of applying the Gabor annulus for bead detection. First, the image is smoothed using a 5×5 rotationally symmetric Gaussian lowpass filter with standard deviation 2, and the first derivative of this image is used to establish the contrast between the bead well and the bead edge. Next, the positive calibrator beads are located using the Gabor annulus method using a series of three kernels with various radii values. The convolution responses of the three filters are normalized and aggregated, and the centroid of the bead is determined from the aggregate response matrix. Once the location of the calibrator beads are determined, the distance between the calibrator beads is used to map out most likely coordinates for the remaining beads. The Gabor annulus method is applied to the remaining beads in the same way as described for the calibrator beads. If the bead outline trace is misaligned with the bead image, a manual input function may be used to draw the coordinates manually.

The "donut region of interest" or "donut ROI" method is a regional pixel analysis technique that attempts to enhance the performance of the pBNC bead-based assay platform. Instead of averaging the pixels of the entire bead (circle ROI method), the donut ROI method excludes pixels in the bead center and focuses on the pixels that form the signal around the edges of the bead.

Our proof of concept experiments have shown that fine-tuning of the donut radius can either lower intra-assay CV or increase signal, allowing for lower limits of detection (defined as 3 standard deviations above concentration zero measurement in a dose curve) or greater sensitivity, respectively. The tradeoff between signal and intra-assay CV is largely application specific (i.e., the requirements of each assay vary depending on the characteristics of the target dynamic range, and our image analysis platform is flexible towards these requirements). Future iterations of the donut method may involve various morphological regions of interest and statistical techniques for improving the performance of the pBNC assay system.

An Image Analysis Tool was developed in MATLAB, and a graphical user interface (GUI) allows the user to analyze the data in a customizable fashion. The MATLAB GUI was compiled as an executable application using MATLAB Compiler, allowing the program to run on any PC without a MATLAB license. To analyze an image, the user clicks the "choose image" button. A window appears for the user to browse for an image to analyze. The pBNC image analysis tool can analyze the following image types: BMP, GIF, HDF, JPEG, PCX, PNG, TIFF, XWD, and others. The current pBNC analyzer prototype exports data in 12-bit TIFF images.

Once the image is selected, the user has the choice of performing background subtraction on the image. Background subtraction is performed by estimating background illumination via a morphological opening operation (erosion followed by dilation, using the same structuring element for both operations). The opening operation has the same effect of removing objects that cannot completely contain the structuring element. Here, we are using a disk-shaped structuring element with predefined radius r, however, other background subtraction methods may be used such as the "rolling ball" method. Also, once the beads are located the median value of the entire image area surrounding the beads may be subtracted from the image to remove background noise from the image.

The image analysis tool also has the ability to analyze images with different magnifications (e.g., 4×, 5×, 10×) and multiple sizes of camera sensors, and the Gabor annulus radius and calibrator bead search coordinates are altered accordingly. The image analysis tool can perform data analysis using various methods including (but not limited to) circle ROI, line profile, and donut ROI methods.

The CV upper limit parameter allows the user to set a limit to the CV such that all pixels within a bead fall within a certain range. This is performed by a stepwise shrinking of the evaluable distribution of pixels. In other words, the population of pixels is iteratively shrunk towards the median as long as the CV upper limit condition is unmet. Typical bead CV is ~30% for beads with high signal. Default CV upper limit is set to 100%.

Figure 8:
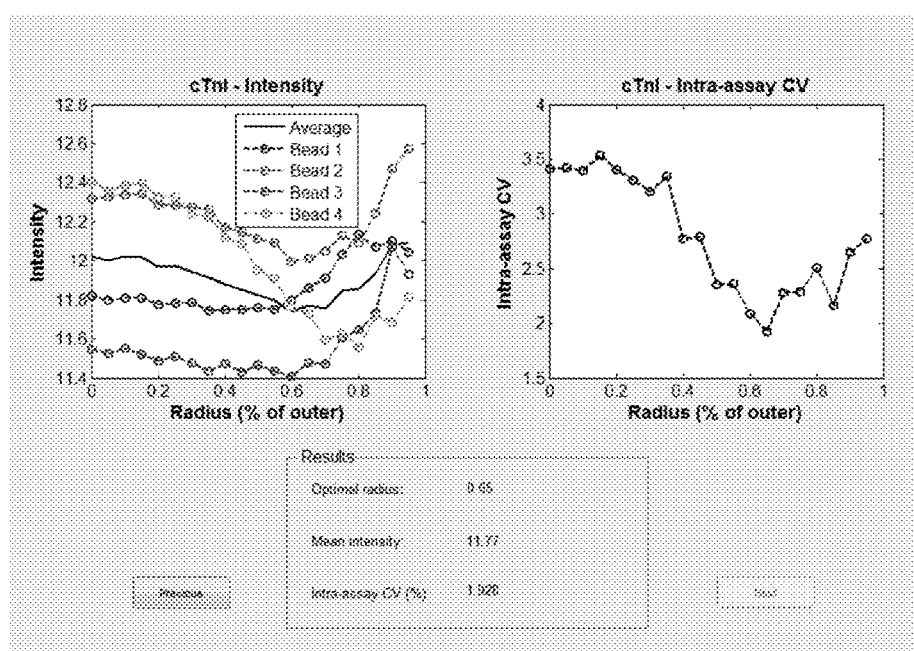
FIG. 8. illustrates an exemplary results window showing intensity and intra-assay CV as a function of donut radius. This exemplary data was obtained using beads conjugated to antibodies for cardiac troponin I (cTnI), and human serum samples.

The analyze function performs the data analysis method, and the export function allows the user to save the results to an Excel file. If the "Optimize radius" button is selected, a results window (e.g., FIG. 8) will show the intensity and intra-assay CV vs. donut radius and select the radius that minimizes the intra-assay CV or that maximizes the intensity. The default save paths and image paths are modifiable in the File tab. Currently, the image analysis program takes ~10 seconds to locate the beads and ~5 seconds to analyze the images (not yet optimized for speed). Future commercial-ready versions of the image analysis software will be performed locally on the analyzer's embedded PC or on a cloud-based server.

We have laid the foundation herein for a fully-integrated bead-based lab-on-a-chip immunoassay platform that has potential to bridge technology gaps necessary to mobilize cardiac biomarker analysis. Toward this goal, we demonstrated the PBNC's ability to take advantage of the versatility of bead-based approach, such as multiplexed analysis and a high redundancy of simultaneous measurements, while making use of the traditional advantages of integrated microfluidics, including ease of use, automated analysis, faster analysis times, low sample and reagent volume consumption, and reduced cost. The strength of the PBNC assay platform lies in its programmable analysis core and modular platform construction, which can be easily re-tasked to new diagnostic modalities.

Here, the device has potential to meet myriad unmet needs in clinical diagnostics; however, considering the global prevalence of cardiovascular disease, we chose the analysis of cardiac biomarkers to demonstrate the analytical capabilities of the platform. High sensitivity, accurate and precise assay performance was achieved four FDA approved cardiac biomarkers, CTnI, CKMB, MYO, and NT-ProBNP, which demonstrates progress toward combining diagnosis, prognosis, and monitoring of therapeutic interventions in a single test.

Low pg/mL detection limits were obtained with less than 10% CV at all concentration levels tested with a total analysis time of 15 minutes. Such low detection limits and high precision demonstrate excellent potential for achieving "high sensitivity" status for the analysis of cardiac troponins at the point-of-care, which is of great interest for early onset diagnosis of AMI.

Finally, the potential clinical utility of the pBNC assay platform was demonstrated by processing human patient samples from confirmed AMI, CHF, and non-case disease state patients, which shows great promise for implementation of the device in "real world" clinical analysis. We thus demonstrated clear progress toward creating a compact field-deployable assay system that has great potential to change the diagnostic paradigm for AMI and other systemic diseases by enabling high sensitivity and high specificity multiplexed immunoassay analysis to the POC.

Each of the following reference is incorporated by reference herein in its entirely.

61/498,761, US20120322682, WO2012154306, WO2012065117, WO2012065025, WO2012021714, WO2007134189, WO2012065025, 61/815,305 filed Apr. 24, 2013.

[1] Goodey, A. et al., "Development of multianalyte sensor arrays composed of chemically derivatized polymeric microspheres localized in micromachined cavities," J. Am. Chem. Soc. 123, 2559-2570 (2001).

[2] Christodoulides, N. et al., "A microchip-based multianalyte system for the assessment of cardiac risk," Anal Chem. 74(13), 3030-3036 (2002).

[3] Christodoulides, N., et al., "Application of microchip assay system for the measurement of C-reactive protein in human saliva," Lab Chip. 5(3), 261-269 (2005).

[4] Rodriguez, W. R., et al., "A Microchip CD4 Counting Method for HIV Monitoring in Resource-Poor Settings," PloS Med. 2(7), 663-672 (2005).

[5] Floriano, P. N., et al., "Membrane-based on-line optical analysis system for rapid detection of bacteria and spores," Biosens Bioelectron. 20(10), 2079-2088 (2005).

[6] Christodoulides, N., et al., "A microchip-based assay for interleukin-6," Meth. Mol. Bio. 385, 131-144 (2007).

[7] Weigum, S. E., Floriano, P. N., Christodoulides, N., and McDevitt, J. T., "Cell-based sensor for analysis of EGFR biomarker expression in oral cancer," Lab Chip 7(8), 995-1003 (2007).

[8] Jokerst, J. V., et al., "Nano-bio-chips for high performance multiplexed protein detection: determinations of cancer biomarkers in serum and saliva using quantum dot bioconjugate labels," Biosens Bioelectron. 24, 3622-3629 (2009).

[9] Christodoulides, N. et al., "Programmable Bio-nano-chip Technology for the Diagnosis of Cardiovascular Disease at the Point-of-care," Method. De Bakey Cardiovasc. J., 1, 6 (2012).

[10] Weigum, S. E., et al., "Nano-bio-chip sensor platform for examination of oral exfoliative cytology," Cancer Prev. Res. 3, 518 (2010).

[11] Raamanathan, A., et al., "Programmable bio-nano-chip systems for serum CA125 quantification: toward ovarian cancer diagnostics at the point-of-care," Cancer Prev. Res. 5(5):706 (2012).

[12] Jokerst J. V., et al., "Programmable nano-bio-chips: multifunctional clinical tools for use at the point-of-care," Nanomedicine 5(1), 143-155 (2010).

[13] Rhodes, Bai: Circle detection using a Gabor Annulus, available at http://www.cs.nott.ac.uk/~aqr/circle/papers/gaborannulus_final.pdf

What is claimed is:

1. An analyzer for a lab card, said analyzer comprising:
a) an optical imaging module located above a sample platform;
b) one or more blister actuators located above said sample platform, each blister actuator having a stepper motor for moving said blister actuator up and down and a force sensor resistor for detecting a force on said blister actuator;
c) a processor operably connected to said optical imaging module and to said blister actuator, wherein said processor controls and collects data from said optical imaging module, and controls said blister actuator;
d) each of components a-c housed inside a housing;
e) said housing further comprising a lab card slot in communication with said sample platform and a user interface, wherein the user interface is in communication with said processor,
wherein said processor accommodates a geometry of a blister on a lab card to adjust a rate of movement of said blister actuator to deliver a constant flow rate of a fluid from said blister.

2. The analyzer of claim 1, wherein said housing further comprises a connector for cables connecting said processor to external display or storage devices.

3. The analyzer of claim 1, wherein said optical imaging module detects fluorescence light signals from a lab card.

4. The analyzer of claim 1, said optical imaging module comprising a microscope, a light source, and a photodetector for detecting light from a lab card.

5. The analyzer of claim 1, said optical imaging module comprising a microscope, a light source, one or more optical filters, and a photodetector for detecting light from a lab card.

6. The analyzer of claim 5, wherein said optical imaging module comprises an LED light source, and a CCD or CMOS camera for detecting fluorescence from a lab card.

7. The analyzer of claim 1, wherein said housing is lightproof when a lab card is inserted into said lab card slot such that external light does not reach said optical imaging module.

8. The analyzer of claim 1, wherein said housing further houses a supply storage container.

9. The analyzer of claim 1, wherein said force sensor resistor detects the top of said blister upon actuation by said blister actuator and detects a controlled burst of the blister and subsequent release of reagents into a lab card.

10. The analyzer of claim 1, wherein said blister actuator movement slows with increasing compression of a rounded blister.

11. The analyzer of claim 1, wherein said blister actuator is semispherical and the movement of the blister actuator slows with increasing compression of a semispherical blister.

12. The analyzer of claim 1, wherein said blister actuator is semispherical and the movement of the blister actuator slows with increasing compression of a semispherical blister according to equation A and B:

$$Q = \frac{dV}{dz}\frac{dz}{dt} \qquad \text{Eq. A}$$

where Q is the desired flow rate, $$\frac{dz}{dt}$$

is me actuation Tale, and $$\frac{dV}{dz} = \frac{(3r - \frac{z}{2})\pi z}{3} - \frac{\pi z^2}{12} \qquad \text{Eq. B}$$

where z is the actuation depth, and r is the radius of said semispherical blister and V is the volume of the blister.

13. The analyzer of claim 1, wherein said processor utilizes Gabor annulus method for automatically locating a bead region of interest in a lab card.

14. The analyzer of claim 1, wherein said processor averages the normalized results from two, three, or multiple Gabor annulus convolutions to improve accuracy of a bead location.

15. The analyzer of claim 1, wherein said processor utilizes a donut region of interest analysis for detection of signals present on a bead in a lab card, and exclude signals from a center of said bead.

16. The analyzer of claim 1, wherein said processor utilizes a donut region of interest analysis to optimize the radius of interest for minimum intra-assay CV or maximum signal intensity.

17. The analyzer of claim 1, wherein said processor utilizes a donut region of interest analysis for detection of signals present on a bead on a lab card, and exclude signals from a center of said bead.

18. The analyzer of claim 1, wherein said processor averages normalized results from two, three, or multiple Gabor annulus convolutions to improve accuracy of bead locations and utilizes a donut region of interest analysis to optimize the radius of interest for minimum intra-assay CV or maximum signal intensity.

19. A method of analyzing a lab card, comprising the steps of:
   a) inserting a lab card having rounded blisters into a card slot located on an external housing, wherein said card slot is in communication with a sample platform, wherein said inserted lab card rests on said sample platform;
   b) compressing said rounded blisters located on said lab card using a blister actuator and stepper motors within said external housing to move said blister actuator vertically, wherein said blister actuator slows said blister actuation with increasing compression by a processor that accommodates a geometry of said rounded blister on said lab card to deliver a constant flow rate of a fluid from said rounded blister;
   c) wherein said compressed blisters release reagents and/or analytes into said lab card;
   d) obtaining optical images of said lab card using an optical imaging module located above said lab card;
   e) processing said optical images on said processor located within said external housing to obtain an assay result; and
   f) displaying said assay result on a display means connected to said processor.

20. The method of claim 19, wherein said lab card includes a bead conjugated to an antibody.

21. The method of claim 20, wherein said processing includes Gabor annulus bead detection for automated location of beads by said processor.

22. The method of claim 21, wherein said processing includes a donut region of interest processing of signal from said bead, ignoring signals from a center of said bead.

23. The method of claim 22, wherein said processor averages the normalized results from two, three, or multiple Gabor annulus convolutions to improve accuracy of the bead location and utilizes the donut region of interest analysis to optimize the radius of interest for minimum intra-assay CV or maximum signal intensity.

24. The method of claim 19, wherein said compressing step b), further comprises lowering the blister actuator until a force sensor resistor detects contact with said rounded blister.

25. The method of claim 24, wherein said processor communicates with said force sensor resistor and said blister actuator while the blister actuator moves vertically toward said rounded blister, wherein the processor recognizes when the blister actuator makes contact with the rounded blister via a signal from the force sensor resistor reaching a voltage threshold.

26. The method of claim 24, wherein said processor communicates with said force sensor resistor and said blister actuator while the blister actuator compresses said rounded blister and stops the blister actuator upon bursting the rounded blister when the signal from the force sensor resistor exhibits a change in voltage signal from sudden pressure release of the rounded blister contents into said lab card.

* * * * *

UNITED STATES PATENT AND TRADEMARK OFFICE
CERTIFICATE OF CORRECTION

PATENT NO. : 10,060,937 B2
APPLICATION NO. : 14/319497
DATED : August 28, 2018
INVENTOR(S) : John T. McDevitt et al.

Page 1 of 1

It is certified that error appears in the above-identified patent and that said Letters Patent is hereby corrected as shown below:

Claim 12, in Column 19, Line 12:
The words "me" and "Tale" should be replaced with "the" and "rate", respectively.

Signed and Sealed this
Ninth Day of October, 2018

Andrei Iancu
*Director of the United States Patent and Trademark Office*